(12) United States Patent
Fowler et al.

(10) Patent No.: US 8,758,267 B2
(45) Date of Patent: Jun. 24, 2014

(54) MODIFIED LANCET CARRIER FOR SINGLE-USE LANCET SENSOR ASSEMBLY

(75) Inventors: James Fowler, Brewster, MA (US); Robert Daggett, Chelmsford, MA (US)

(73) Assignee: Nova Biomedical Corporation, Waltham, MA (US)

( * ) Notice: Subject to any disclaimer, the term of this patent is extended or adjusted under 35 U.S.C. 154(b) by 467 days.

(21) Appl. No.: 12/405,688

(22) Filed: Mar. 17, 2009

(65) Prior Publication Data

US 2010/0241030 A1 Sep. 23, 2010

(51) Int. Cl.
*A61B 5/00* (2006.01)
*A61B 17/32* (2006.01)

(52) U.S. Cl.
USPC ........... 600/583; 600/300; 600/573; 600/575; 600/576; 600/577; 600/578; 600/579; 600/584; 606/181; 606/182; 606/183

(58) Field of Classification Search
USPC ............................ 600/573, 583; 606/181, 182
See application file for complete search history.

(56) References Cited

U.S. PATENT DOCUMENTS

| | | | | |
|---|---|---|---|---|
| 4,360,016 A | * | 11/1982 | Sarrine | 600/576 |
| 4,637,403 A | | 1/1987 | Garcia et al. | |
| 4,661,319 A | * | 4/1987 | Lape | 422/100 |
| 4,787,398 A | | 11/1988 | Garcia et al. | |
| 5,279,294 A | | 1/1994 | Anderson et al. | |
| 5,423,847 A | | 6/1995 | Strong et al. | |
| 5,628,765 A | | 5/1997 | Morita | |
| 5,707,384 A | | 1/1998 | Kim | |
| 5,755,733 A | | 5/1998 | Morita | |
| 5,971,941 A | | 10/1999 | Simons et al. | |
| 6,071,294 A | * | 6/2000 | Simons et al. | 606/181 |
| 6,168,606 B1 | | 1/2001 | Levin et al. | |
| 6,283,982 B1 | * | 9/2001 | Levaughn et al. | 606/172 |
| 6,322,574 B1 | * | 11/2001 | Lloyd et al. | 606/181 |
| 6,332,871 B1 | | 12/2001 | Douglas et al. | |
| 6,514,270 B1 | | 2/2003 | Schraga | |
| 6,530,892 B1 | | 3/2003 | Kelly | |
| 6,561,989 B2 | | 5/2003 | Whitson | |
| 6,607,658 B1 | | 8/2003 | Heller et al. | |

(Continued)

FOREIGN PATENT DOCUMENTS

EP 1285629 A1 2/2003
WO 9742888 11/1997

(Continued)

OTHER PUBLICATIONS

PCT Search Report issued Aug. 24, 2010 PCT/IB2009/056006.

(Continued)

*Primary Examiner* — Sean Dougherty
(74) *Attorney, Agent, or Firm* — Robert R. Deleault, Esq.; Mesmer & Deleault, PLLC (57) ABSTRACT

A lancet carrier for an integrated lancet sensor assembly incorporating a lance cover includes an elongated body with a bottom, an open top, a body open end and a body closed end, a lancet-receiving recess with a recess bottom surface, the recess extending between the open end and the closed end, and a trough-forming member forming a trough with a trough open end in communication with the body open end, the trough-forming member longitudinally extending a predefined distance along the bottom from the body open end, the trough replacing a portion of the recess bottom surface at the body open end.

11 Claims, 9 Drawing Sheets

(56) References Cited

U.S. PATENT DOCUMENTS

| | | |
|---|---|---|
| 6,620,112 B2 | 9/2003 | Klitmose |
| 7,192,405 B2 | 3/2007 | DeNuzzio et al. |
| 7,604,777 B2 * | 10/2009 | Columbus .................... 422/102 |
| 2002/0052618 A1 | 5/2002 | Haar et al. |
| 2002/0082522 A1 | 6/2002 | Douglas et al. |
| 2002/0130042 A1 | 9/2002 | Moermann et al. |
| 2002/0168290 A1 * | 11/2002 | Yuzhakov et al. ............. 422/56 |
| 2002/0177761 A1 | 11/2002 | Orloff et al. |
| 2003/0050573 A1 | 3/2003 | Kuhr et al. |
| 2003/0050656 A1 | 3/2003 | Schraga |
| 2003/0083685 A1 | 5/2003 | Freeman et al. |
| 2003/0083686 A1 | 5/2003 | Freeman et al. |
| 2003/0144608 A1 | 7/2003 | Kojima et al. |
| 2003/0171696 A1 | 9/2003 | Dosmann |
| 2004/0064068 A1 | 4/2004 | DeNuzzio et al. |
| 2004/0102802 A1 * | 5/2004 | Marshall ...................... 606/182 |
| 2004/0225311 A1 | 11/2004 | Levaughn et al. |
| 2005/0149090 A1 | 7/2005 | Morita et al. |
| 2005/0177183 A1 | 8/2005 | Thorne et al. |
| 2005/0234368 A1 | 10/2005 | Wong et al. |
| 2005/0251064 A1 | 11/2005 | Roe |
| 2005/0277850 A1 | 12/2005 | Mace et al. |
| 2005/0283094 A1 | 12/2005 | Thym et al. |
| 2006/0064035 A1 * | 3/2006 | Wang et al. .................... 600/583 |
| 2006/0241517 A1 * | 10/2006 | Fowler et al. ................. 600/583 |
| 2007/0149897 A1 | 6/2007 | Ghesquiere et al. |
| 2010/0160943 A1 * | 6/2010 | Lamps et al. ................. 606/182 |

FOREIGN PATENT DOCUMENTS

| | | |
|---|---|---|
| WO | 0205872 A2 | 1/2002 |
| WO | 02078533 A2 | 10/2002 |
| WO | 02078533 A3 | 10/2002 |
| WO | 02100254 A2 | 12/2002 |
| WO | 02100254 A3 | 12/2002 |
| WO | 03015627 A2 | 2/2003 |
| WO | 2005046477 A2 | 5/2005 |
| WO | 2005107595 A1 | 11/2005 |
| WO | 2006013532 A1 | 2/2006 |

OTHER PUBLICATIONS

Chinese patent office of co-pending application, office action dated Apr. 15, 2013 with English translation.

* cited by examiner

MODIFIED LANCET CARRIER FOR SINGLE-USE LANCET SENSOR ASSEMBLY

BACKGROUND OF THE INVENTION

1. Field of the Invention

The present invention relates generally to a lancet device. Particularly, the present invention relates to a single use lancet device. More particularly, the present invention relates to a lancet carrier for a single use, integrated lancet sensor assembly.

2. Description of the Prior Art

Lancets are well-known devices commonly used in the medical field to make small punctures in a patient's skin in order to obtain samples of blood. They are utilized in hospitals, other medical facilities and by private individuals such as diabetics for testing droplets of blood for various analytes. Typically, lancets are used only once in order to reduce the risk of HIV, hepatitis and other bloodborne diseases. The needle of these devices is driven into the patient's skin by a small spring that is cocked by a technician or user prior to use. The needle is covered with a protective, safety cap that keeps the end of the lancet sterile and is removed before use.

There are a variety of lancet devices that are available for utilization by patients and/or practitioners in a variety of different circumstances. One variety is configured for multiple and/or repeated uses. This variety typically includes a lancet injector that projects a lancet toward the skin of a patient that is pushed by the user. More commonly, the lancet device effectively encases and fires the lancet into the patient's skin in order to puncture in an accurate, standardized and consistent manner. The lancet injector may also be provided with an adaptor cap to control and adjust the depth of penetration of the needle of the lancet.

Another variety is configured for single use where the entire device is discarded after use. Typically, these devices include a housing that contains and directs or drives a piercing tip into the patient's skin and then is discarded along with the used lancet. Such devices are effective for achieving the piercing of the skin required for effective operation. These single-use, disposable devices, however, typically do not incorporate a large number of safety features to ensure safe use and disposal of the device. A major disadvantage of such devices is that they can be inadvertently re-used. The configuration of these devices is such that a user can re-cock the device and allow for subsequent and inappropriate use of a contaminated lancet.

There have been some devices developed that affirmatively prevent re-use of a single-use lancet. U.S. Pat. No. 5,423,847 (1995, Strong et al.) discloses a safe lancet injector. The safe lancet injector for use with a lancet and an isolating platform to obtain blood samples for diagnostic purposes. The lancet injector uses two elastomeric bands to push the lancet forward and to rapidly withdraw the needle from the skin. It further includes an interlocking mechanism that completely precludes a lancet from being used more than once, which causes the used lancet to be ejected before cocking/arming the lancet injector can be performed.

U.S. Pat. No. 6,168,606 (2001, Levin et al.) discloses a single-use, spring-driven lancet device. The device is pre-cocked during assembly so that the user needs only to remove the safety cap prior to use. A thin plastic fiber connection between the pull-tab and the needle safety cap prevents any compressive force from being applied to the drive spring, which prevents recocking/re-arming of the device.

U.S. Pat. No. 6,514,270 (2003, Schraga) discloses a single use lancet device having a housing, a lancet with a piercing tip movably disposed in the housing and structured to move between a cocked orientation and a piercing orientation, and a driving assembly structured to move the lancet into the piercing orientation. A retention member and an engagement hub are provided and structured to cooperatively engage with one another when the lancet is disposed into the cocked orientation until released by an actuation assembly. The actuation assembly is structured to move between an actuated and an un-actuated orientation. Movement of the actuation member into the actuated orientation releases the retention member and the engagement hub from their cooperative engagement with one another resulting in the movement of the lancet into the piercing orientation. A restrictor assembly prevents the actuation assembly from moving out of the actuated orientation and prevents re-firing of the lancet using the actuation assembly.

These devices, however, are only lancet devices and must be used with separate test strips for making an analyte determination on the sample of blood produced by the lancet device.

There have also been developed integrated lancet and sensor devices that combine the lancet and test strip into a single package. These integrated devices are typically used with a lancet injector where the integrated lancet and test strip is removed from the lancet injector and connected to a meter after acquisition by the test strip of the blood sample produced by the lancet, or used with a meter with built-in lancet injector.

One such integrated device is disclosed in U.S. Patent Application Publication 2007/0149897 by Ghesquiere et al. The device is an integrated lancet and testing striplet for measuring a body analyte level in a health care regimen that includes a lancet needle and an analyte sensor coupled together. A lancet body includes a sensor receiving end and a lancet end. The lancet needle is coupled with and protruding from the lancet end. An optional lancet cap may secure the lancet. The sensor is coupled to the sensor receiving end of the lancet body. The integrated device is positioned within a rotating cradle and, during the assay or after completion of the assay, the cradle is rotated by mechanical transmission to position the lancet for re-attaching the protective cover to the used lancet of the lancet-test strip combination.

U.S. Patent Application Publication 2006/0020228 (2006, Fowler et al.) discloses an integrated lancet and test strip. The assembly includes a lancet disposed within a lancet enclosure where the lancet moves between a retracted position and an extended position out of a needle end of the lancet enclosure, and an elongated test strip having a sample receiving end disposed at the needle end of the lancet enclosure. After piercing the skin, the lancet is retracted into the lancet enclosure so that it is not exposed to prevent accidental piercing.

U.S. Patent Application Publication 2006/0241517 (2006, Fowler et al.) discloses an integrated lancet and test strip. The lancet assembly has a lancet member with a lance, a lancet body having a drive wing extending outwardly from a side, and a sinuous portion, and an elongated lancet assembly carrier having a lancet member recess to contain the lancet member. The lance has a lance cover for maintaining sterility of the lance. The lancet carrier has an open end, a closed end, a side elongated opening for receiving the drive wing therethrough, and an anchoring member operatively connected to the end of the sinuous portion. The lancet carrier also included optional side notches near the closed end to provide additional retention means for retaining the lancet sensor assembly when inserted into a meter.

U.S. Patent Application Publication 2003/0144608 (2003, Kojima et al.) a discloses a lancet integrated sensor. The lancet integrated sensor includes a long and narrow strip-shaped sensor, a lancet, a cover plate with a hollow space or recess that houses a greater part of the lancet, and a protection cover into which the needle tip of the lancet is pressed. The cover plate and strip-shaped sensor are bonded to each other. The lancet includes a metal needle and a connector end portion that projects from the rear of the assembly to be engaged with a driving means of the measuring device. The protection cover is removed during measurement.

These integrated lancet and test strip/sensor devices are typically inserted into a measuring device before removing the lance/needle cover from the lance/needle. When removing the lance cover from the integrated lancet and sensor device, a user pulls, twists and bends the lance cover to separate it from the lancet/needle body. The pulling, twisting and bending action performed by a user to remove the lance/needle cover causes, in some devices, the lancet to be pulled and positioned at its furthest extension relative to the lancet carrier before the lance cover can be twisted and bent for removal. A major disadvantage of these integrated lancet and test strip devices is that, if care is not taken by the user, the twisting and bending action applies a torquing force against and perpendicular to the plane of the sensor strip causing the sensor strip to bend in the area of the measuring electrodes which damages the sensor strip.

Another disadvantage of the prior art is the latching mechanism that retains the integrated lancet sensor within the measuring meter. The prior art involves a receiver in the measuring meter that captures either a curved notch on a side of the lancet carrier near the electrical contacts of the sensor or the end of the lancet opposite the needle. In either case, the removal of the lance/needle protective cover after insertion of the integrated lancet sensor device into the measuring meter can cause the lancet carrier or the lancet end to disengage from their respective receivers.

Therefore, what is needed is an integrated lancet sensor device having a lance protective cover that overcomes the disadvantages of the prior art.

SUMMARY OF THE INVENTION

It is an object of the present invention to provide an integrated lancet sensor device with a lance protection cover. It is another object of the present invention to provide an integrated lancet sensor device with a lance protection cover that reduces the likelihood of damage to the sensor when the lance protection cover is removed. It is a further object of the present invention to provide a lancet sensor device that cannot be accidentally removed from a measuring meter while removing the lance protection cover. It is still another object of the present invention to provide a mechanism for identifying the type of analyte the sensor portion of the integrated lancet sensor device is capable of measuring.

The present invention achieves these and other objectives by providing an integrated lancet sensor cartridge having sensor strip, a lancet disposed within a lancet carrier, and a lance protection cover over the lance of the lancet that reduces the likelihood of damage to the sensor strip when the lance protection cover is removed for use. In one embodiment of the present invention, the integrated lancet sensor cartridge has a lancet carrier that includes an elongated body with a bottom, an open top, a body open end, and a body closed end. The carrier body includes a lancet-receiving recess with a recess bottom surface where the recess extends between the body open end and the body closed end. At the body open end, there is a trough-forming member that forms a trough with a trough open end in communication with the body open end. The trough-forming member longitudinally extends a predefined distance along the bottom of the carrier body from the body open end. The trough replaces a portion of the recess bottom surface at the body open end.

In another embodiment of the present invention, the trough of the lancet carrier has a semi-circular shape.

In another embodiment of the present invention, the lancet carrier has a plurality of transverse ridges and valleys formed in an outside surface of a side of the lancet carrier adjacent the open end.

In another embodiment of the present invention, the lancet carrier has an external bottom rib connected on one end to the trough-forming member. The external bottom rib extends longitudinally along a major portion of an outside bottom surface of the lancet carrier. A lancet carrier retaining notch is formed laterally in the external bottom rib and includes a carrier locking surface transverse to the longitudinal axis of the external bottom rib. Preferably, the external bottom rib is located along the longitudinal center line of the lancet carrier.

In still another embodiment of the present invention, the lancet carrier has an aperture formed in the bottom adjacent the closed end. The aperture is used to expose a bottom surface of the sensor strip. The bottom surface of the sensor strip has a configuration that enables a measuring meter to identify the type of analyte the sensor strip is capable of measuring and to accordingly select the programs, algorithms, measurement criteria, and the like for use with the inserted strip.

In another embodiment of the present invention, the integrated lancet sensor device has a lancet carrier that includes an elongated body with a bottom, an open top, a body open end, and a body closed end. The carrier body includes a lancet-receiving recess with a recess bottom surface where the recess extends between the body open end and the body closed end. An external bottom rib extends longitudinally along a major portion of an outside bottom surface of the lancet carrier. A lancet carrier retaining notch is formed laterally in the external bottom rib and includes a carrier locking surface transverse to the longitudinal axis of the external bottom rib. Preferably, the external bottom rib is located along the longitudinal center line of the lancet carrier.

In still another embodiment of the present invention, the lancet carrier has a trough-forming member that forms a trough with a trough open end in communication with the body open end. The trough-forming member longitudinally extends a predefined distance along the bottom of the carrier body from the body open end. The trough replaces a portion of the recess bottom surface at the body open end.

In yet another embodiment of the present invention, a method of reducing damage to a sensor strip in an integrated lancet sensor assembly having a lancet carrier with a recess containing the lancet is provided. The method includes forming a lancet carrier having a trough-forming member that longitudinally extends a predefined distance along a bottom of the lancet carrier from an open end. The trough formed by the trough-forming member replaces a portion of a recess bottom surface of the recess at the open end. The trough enables application of a downward force onto a lance protective cover to be applied for removing the lance protective cover without the edge at the open end of the lancet carrier becoming a fulcrum at a location along the lance protection cover causing the lance protective cover to become a lever. If the lance protective cover becomes a lever, it causes an upward force against the sensor strip at the junction where the lancet protective cover separates from the lancet body. The lever action against the sensor strip damages the sensor strip, which then fails to operate properly.

DETAILED DESCRIPTION OF THE PREFERRED EMBODIMENT

Figure 1:
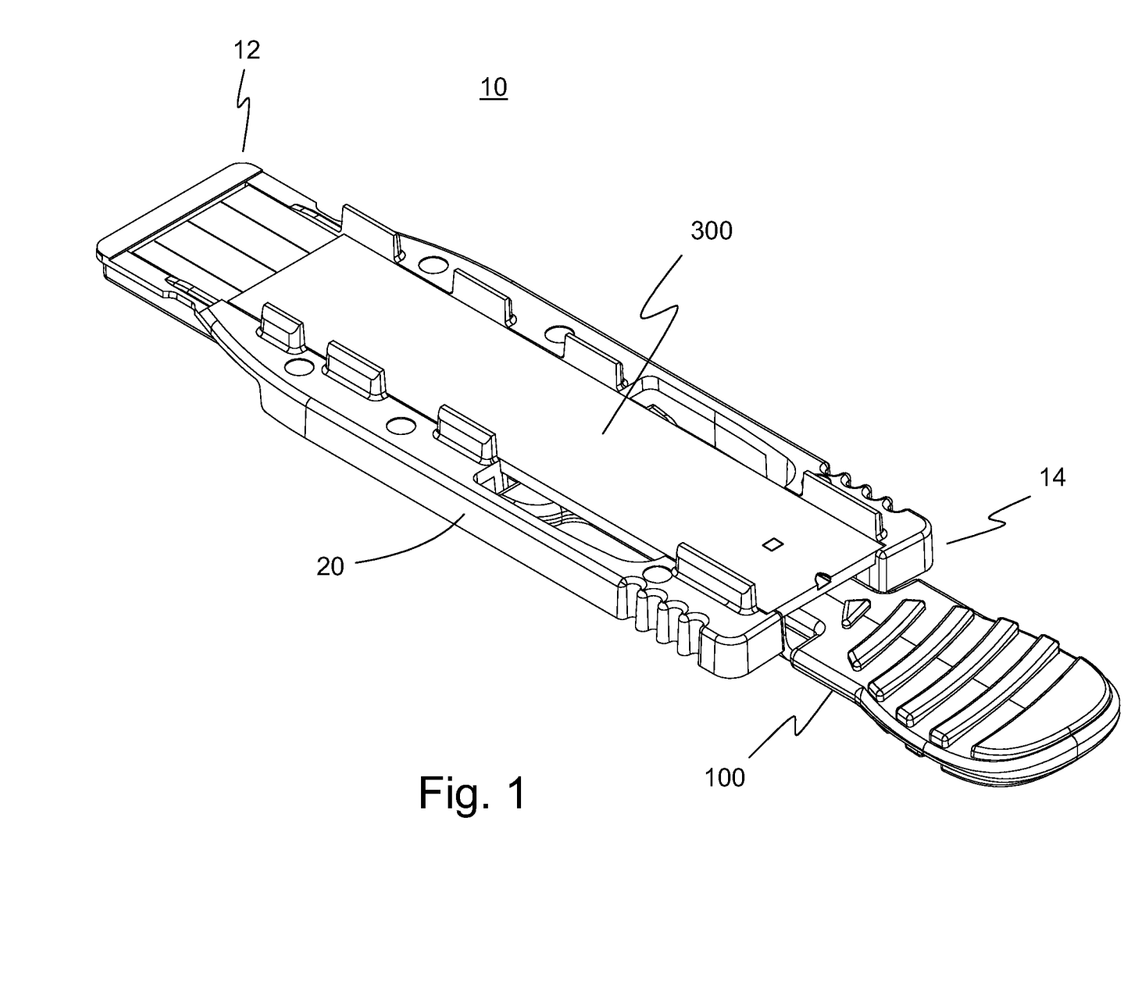
FIG. 1 is perspective, top view of one embodiment of the present invention showing an integrated lancet sensor cartridge.

The preferred embodiment(s) of the present invention is illustrated in FIGS. 1-15. FIG. 1 illustrates one embodiment of a single-use, integrated, lancet sensor cartridge 10 of the present invention for use with a multi-use lancet driver assembly and meter. Lancet cartridge 10 is a single, disposable, one-time use, integrated analytical device that combines a needle component for lancing a specimen and an analyte measuring sensor strip 300 for receiving a fluid sample from the lanced specimen. Lancet cartridge 10 is used in conjunction with a meter by inserting the lancet cartridge 10 into a cartridge receiving port on the meter. A lancet driver assembly is enabled, which when activated, engages the needle component to perform the specimen lancing function. The meter has an electrical coupler that electrically connects to the sensor strip in order to make the analyte measurement. The electrical coupler will be described more fully later.

Lancet cartridge 10 includes a lancet carrier 20, a lancet 100, and a sensor test strip 300. Lancet cartridge 10 has a closed end 12 that is captured by the electrical coupler of the meter and an open end 14 where the specimen lancing and sample acquisition is performed.

Figures 2, 3:
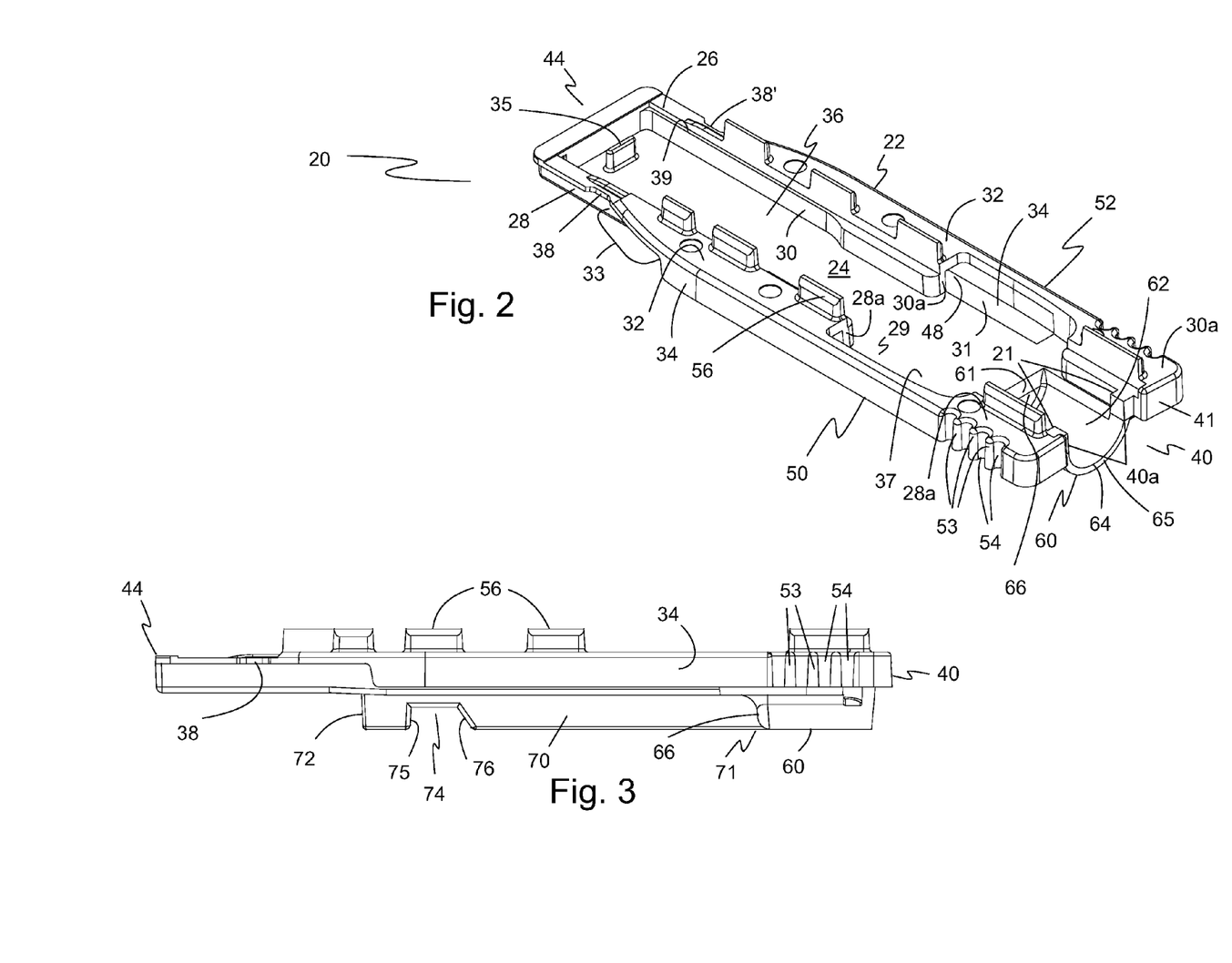
FIG. 2 is a perspective, top plan view of the present invention showing one embodiment of a lancet carrier.
FIG. 3 is a side view of the lancet carrier shown in FIG. 2.

Turning now to FIG. 2, there is illustrated one embodiment of lancet carrier 20. Lancet carrier 20 is an elongated body 22 having a bottom 24, an open top 26, a first side wall 28, a second side wall 30, a body open end 40, and a body closed end 44 that defines a lancet-receiving recess 36. Lancet-receiving recess 36 extends between body open end 40 and body closed end 44 and has a recess bottom surface 37. First and second side walls 28, 30 have a first elongated side opening 29 and a second elongated side opening 31, respectively. First side wall 28 and second side wall 30 extend vertically from bottom 24 into a top planar surface or shelf 32 that laterally extends outwardly from lancet-receiving recess 36. A predefined distance from body closed end 44, shelf 32 on each side of lancet carrier 20 widens through a transition zone 33 and then has a downwardly projecting wall portion 34 that extends past first and second elongated side openings 29, 31. First and second side walls 28, 30, shelf 32 and wall portion 34 form lancet driver slots or channels 48 that together define first and second wing guards 50, 52. Wall portion 34 merges into first and second side wall portions 28a, 30a, respectively. First and second wall portions 28a, 30a are thicker than first and second side walls 28, 30 adjacent body closed end 44 and typically has a thickness substantially equal to wall portion 34, driver slot 48 and first and second side walls 28, 30 adjacent body closed end 44. At the junction of first and second side walls 28, 30 and shelf 32, there is formed a recessed ledge 39. Recessed ledge 39 provides a support surface for the longitudinal side peripheral edges of sensor strip 300.

Formed into shelf 32 at least on first side wall 28 adjacent body closed end 34 is side notch 38. Side notch 38 receives a retaining mechanism (shown in FIGS. 14 and 15) incorporated in the electrical coupler of the meter to capture lancet cartridge 10. Lancet carrier 20 may optionally include a second side notch 38' formed into second side 30 to provide better retention of the captured lancet cartridge 10 within the meter. A plurality of retaining tabs 56 extend upwardly from shelf 32 adjacent recessed ledge 39. Retaining tabs 56 are bendable and/or deformable in order to lock sensor strip 300 into lancet carrier 20.

One of the unique features of lancet carrier 20 is the inclusion of a trough-forming member 60 that forms a trough 62 with a trough wall 65, an open trough end 64 that is in communication with body open end 40 and a trough closed end 66 transverse to trough wall 65. Trough closed end 66 is directly connected to bottom 24. Trough-forming member 60 longitudinally extends a predefined distance along bottom 24 from body open end 40 and terminates in a transverse wall 61. In the preferred embodiment, trough 62 extends from body open end 40 to a point that is approximately parallel to the end of first and second side openings 29 and 31 where wall portion 34 merges into first and second wall portions 28a, 30a. Trough 62 replaces a portion of recess bottom surface 37 adjacent body open end 40.

Another unique feature of lancet carrier 20 is the inclusion of a plurality of ridges 53 and grooves 54 formed into outside wall surfaces 28b, 30b of first and second wall portions 28a, 30a, respectively. The plurality of ridges 53 and grooves 54 provide a friction, non-slip surface for holding lancet cartridge 10 when inserting or removing lancet cartridge 10 from the meter. The plurality of grooves 54 provides spaces into which the skin of a user's finger and thumb easily conforms when grasping the lancet cartridge 10 providing a non-slip grip. Lancet carrier 20 may be made of metal or a plastic material such as, for example, polyvinyl chloride, polycarbonate, polysulfone, nylon, polyurethane, cellulose nitrate, cellulose propionate, cellulose acetate, cellulose acetate butyrate, polyester, acrylic, and polystyrene.

First and second side openings 29, 31 are sufficiently elongated to allow the lancet 100 to move between a retracted and resting orientation and an exposed piercing orientation.

FIG. 3 is a side view of the embodiment of lancet carrier 20 shown in FIG. 2. This view illustrates yet another unique feature of the lancet carrier 20 of the present invention. Although lancet cartridge 10 includes a side notch 38 that is captured by the electrical coupler of the meter, lancet cartridge 10 can still be easily removed from the meter. To prevent any inadvertent removal of cartridge 10 from the meter, lancet carrier is configured to prevent such a mishap. Lancet carrier 20 further includes an external bottom rib 70 connected on a first rib end 71 to trough-forming member 60 and extending along a major portion of bottom 24 to a second rib end 72. Bottom rib 70 has a carrier retaining notch 74 formed in bottom rib 70. Carrier retaining notch 74 includes a carrier locking surface 75 and a front notch surface 76. Carrier locking surface 75 is transverse to the longitudinal axis of external bottom rib 70 and substantially perpendicular to bottom 24 to enhance retention by a cartridge lock within the meter. Front notch surface 76 angles away from carrier locking surface 75 to provide a sliding surface against which the carrier lock of the meter encounters during insertion of the lancet cartridge 10 into the meter to facilitate moving the carrier lock into the locking position against carrier locking surface 75. Carrier retaining notch 74 when coupled to a cartridge lock of the meter prevents the lancet cartridge 10 from being inadvertently removed from the meter without the user purposely disengaging the cartridge lock.

Figure 4:
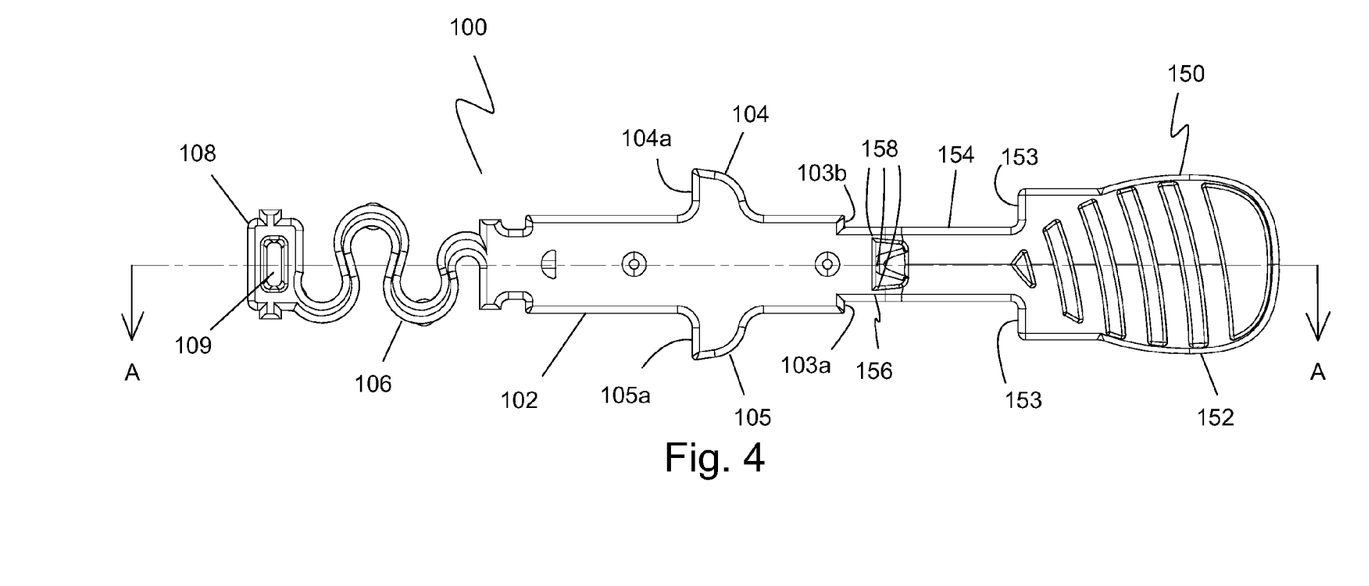
FIG. 4 is a top plan view of one embodiment of a lancet assembly of the present invention showing a lancet body, a biasing member and an optional safety cap
Figure 5:
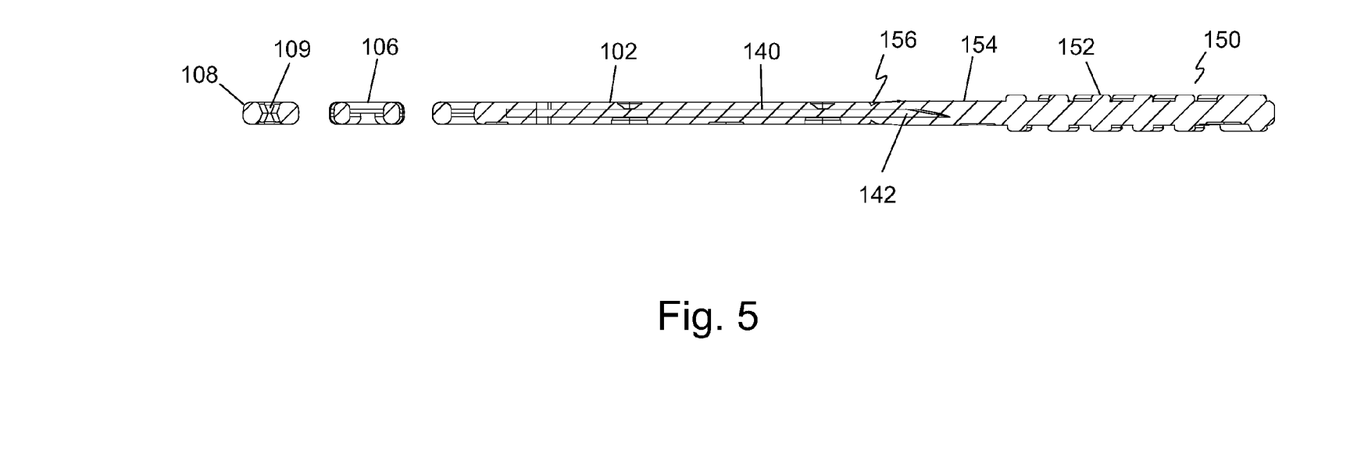
FIG. 5 is a cross-sectional view of the lancet assembly taken along line A-A shown in FIG. 4.

FIG. 4 illustrates a top view of one embodiment of lancet 100. Lancet 100 includes a lancet body 102 having first and second drive wings 104, 105, a biasing member 106, a lancet needle 140 (shown in FIG. 5), and an optional needle safety cap 150. Biasing member 106 is directly connected to lancet body 102 on one end and includes an anchoring component 108 at the opposite end. Anchoring component 108 preferably includes a through opening 109 that receives a retaining flange 35 of lancet housing 20. Anchoring component 108 fixes one end of lancet 100 so that biasing member 106 functions as intended, which is to pull the lancet body 102 and lancet needle 140 back into a retracted orientation within lancet housing 20 after having been moved to the exposed piercing orientation by the driver piston within the meter. As illustrated in FIGS. 1 and 4, safety cap 150 has a wider portion 152 that abruptly changes to a narrower portion 154. Narrower portion 154 is sized to slidably fit within body open end 40 of lancet carrier 20. Narrower portion 154 is attached to lancet body 102 by a frangible connection 156. Frangible connection 156 preferably has three, separate neck portions 158 that are forcibly separated by a user from lancet body 102 to expose the piercing end 142 of lancet needle 140. Safety cap 150 has a butting surface 153 at the transition between wider portion 152 and narrower portion 154. Butting surface 153 prevents compression of biasing member 106 when lancet 100 is mounted within lancet carrier 20 by contacting carrier open end wall 41 if lancet 100 is inadvertently pushed into carrier 20 by an unexpected force. First and second drive wings 104, 105 also have wing but surfaces 104a and 105a, respectively, that also prevent compression of biasing member 106 when lancet 100 is mounted within lancet carrier 20 by contacting carrier wall ends 28b, 30b. FIG. 5 is a cross-sectional view of lancet 100 shown in FIG. 4. FIG. 5 shows the relative position of lancet needle 140 within lancet body 102 and the frangible connection 156 where safety cap 150 is separated from body 102 exposing lancet needle 140.

Figure 6:
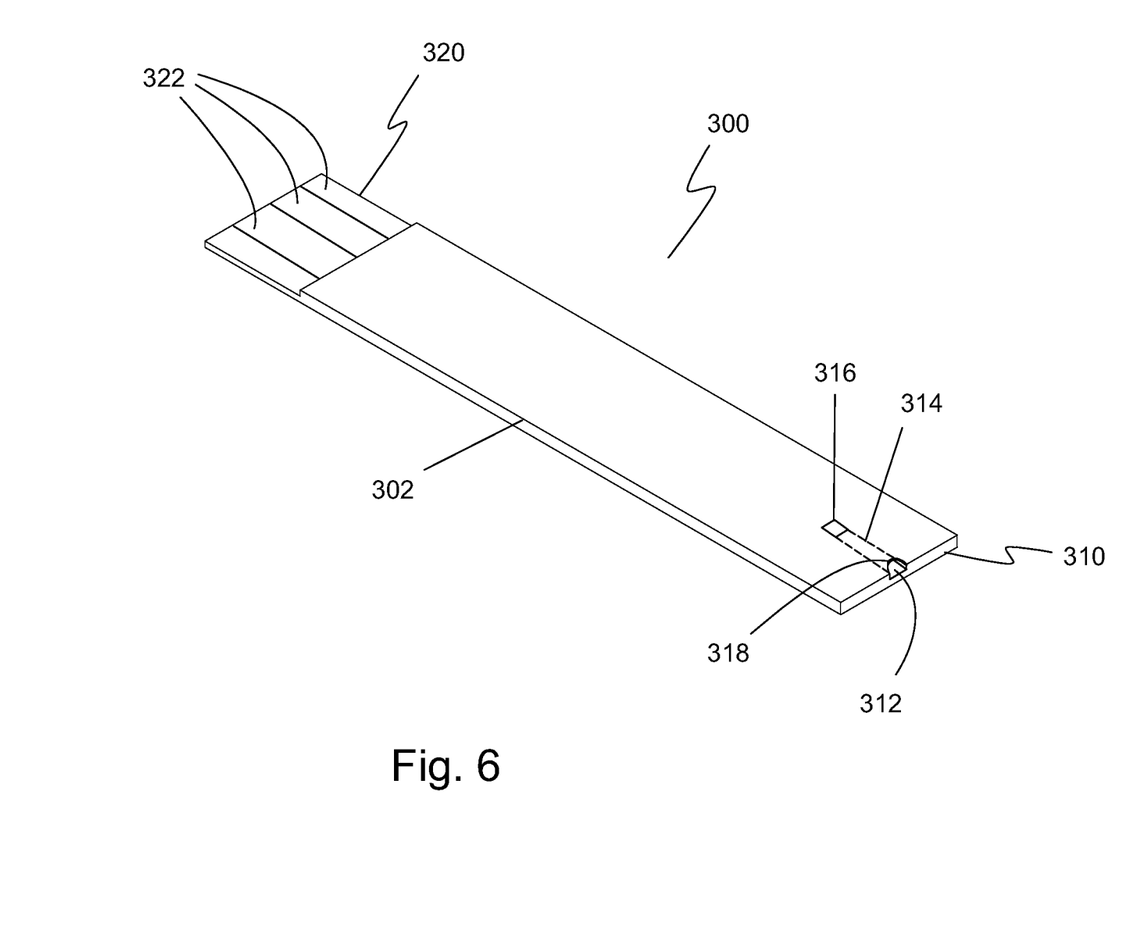
FIG. 6 is a perspective, top view of one embodiment of the sensor strip of the integrated lancet sensor cartridge of the present invention showing the elongated body, the sample receiving end and the electrical connector end.

Turning now to FIG. 6, there is illustrated one embodiment of sensor test strip. Sensor test strip 300 is a disposable sensor strip capable of measuring the concentration of a predefined analyte in a liquid sample. An example of such a sensor test strip is a disposable glucose test strip for measuring blood glucose. However, disposable strips designed to measure other analytes may also be incorporated into lancet sensor cartridge 10 as well as sensor strips capable of measuring multiple analytes. Sensor test strip 300 has an elongated body 302 with a sample receiving end 310 and a connector end 320. Connector end 320 has one or more electrical contact pads 322 for coupling the analyte electrodes to a meter (not shown). Sample receiving end 310 includes a sample inlet 312, a sample chamber 314 that contains the analyte measuring electrodes (not shown) within a capillary-sized, elongated tube and a vent 316 through which air escapes as it is displaced within sample chamber 314 when a sample, which fills sample chamber 314 by capillary action, is applied to sample inlet 312. A notch 318 is preferably incorporated within the roof of sample chamber 314 at sample receiving end 310 to prevent inadvertent blocking of the sample inlet 312 by the sample applicator such as a finger that would cause the sample to stop proceeding along sample chamber 314 and fail to cover the analyte electrodes leading to an erroneous result.

Figure 7A:
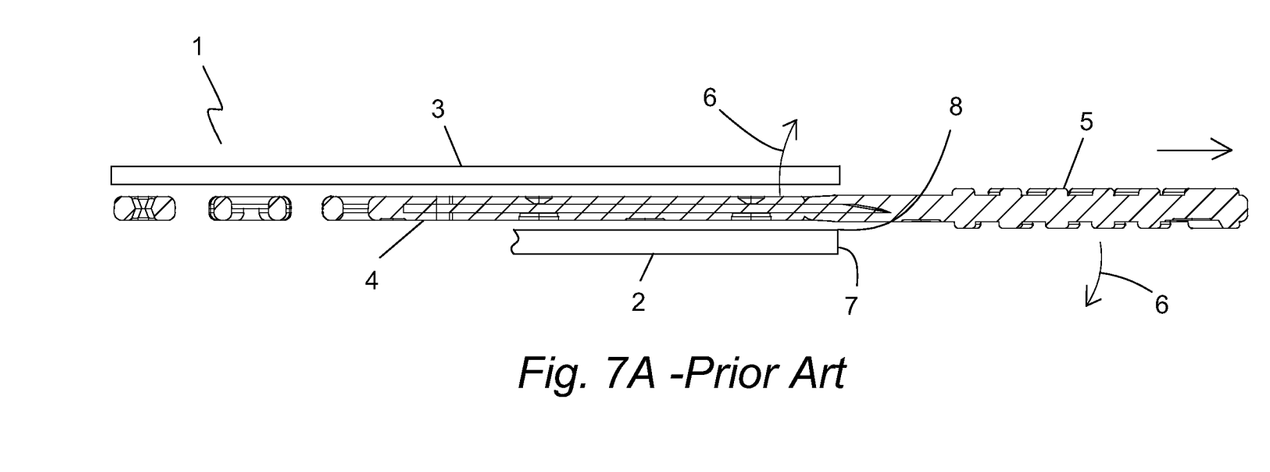
FIG. 7A is an enlarged, simplified, partial cross-sectional view of a conventional integrated sensor strip showing the sensor strip, the lancet assembly and a portion of the lancet carrier.
Figure 7B:
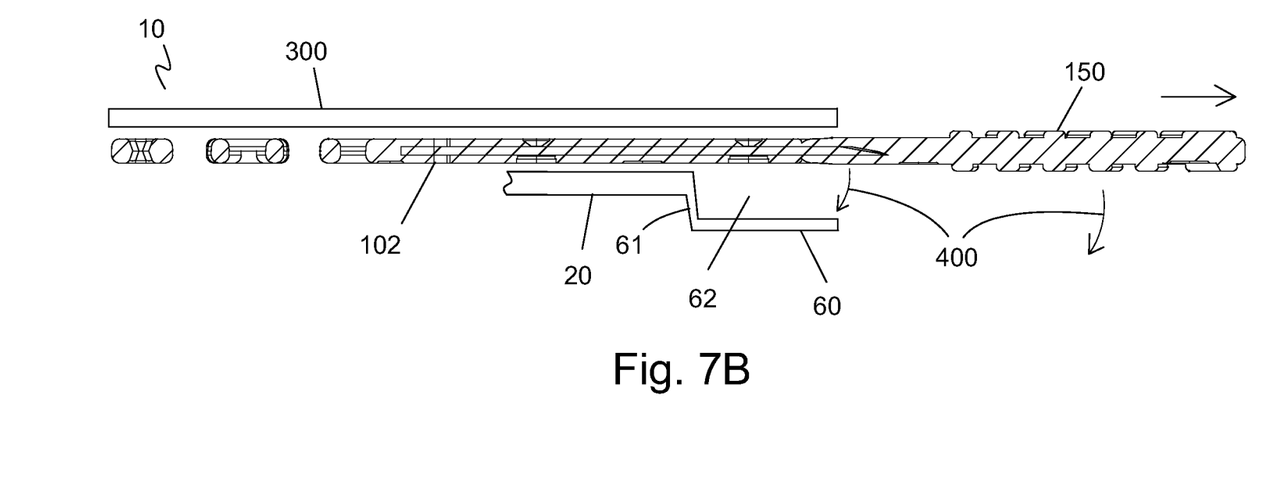
FIG. 7B is an enlarged, simplified, partial cross-sectional view of one embodiment of an integrated lancet sensor cartridge showing the sensor strip, the lancet assembly and a portion of the lancet carrier with a trough at the lancet carrier open end.

FIGS. 7A and 7B illustrate one of the advantages of the feature of lancet carrier 20 previously discussed relate to trough forming member 60. FIG. 7A shows a simplified cross-sectional and enlarged view (not to scale) of a prior art lancet cartridge 1 with a sensor strip 3 enclosing a lancet 4 with a safety cap 5 within a lancet carrier 2. The position of lancet 4 relative to lancet carrier 2 and sensor strip 3 represents the extended position when a user pulls on the safety cap 5 to remove it prior to use since nothing prevents the biasing member 106 from stretching. It is the front body shoulders 103a, 103b (shown in FIG. 4) that engage body shoulder stops 21 of lancet carrier 20 (shown in FIG. 2) that prevents a user from over-extending and damaging biasing member 106. Arrows 6' and 6" indicate the torquing motion imparted to lancet carrier 2 and sensor strip 3 when safety cap 5 is removed. Because sensor strip 3 is thinner than the end 7 of lancet carrier 20, end 7 does not flex or flexes less than sensor strip 3. The result is that the edge 8 of end 7 acts as a fulcrum and causes the lance body 102 to apply a localized force against sensor strip 3 in the area of the analyte electrodes due to the pivoting and torquing action applied. This localized force can and has caused damage to sensor strip 3 rendering it unusable.

On the other hand, FIG. 7B illustrates an enlarged, cross-section view (not to scale) of lancet cartridge 10 with sensor strip 300 enclosing lancet body 102 with a safety cap 150 within lancet carrier 20 and the advantage of incorporating trough forming member 60, which terminates in a transverse wall 61. When the same pivoting and torquing action is applied to remove safety cap 150, the trough 62 allows lancet body 102 to bend in a downward direction into trough 62 illustrated by arrows 400. Because there is no edge to prevent the lancet body 102 from bending, there is no fulcrum to act on lancet body 102 and cause it to apply a localized force against sensor strip 300. Thus, damage to sensor strip 300 is prevented.

Figures 8, 9:
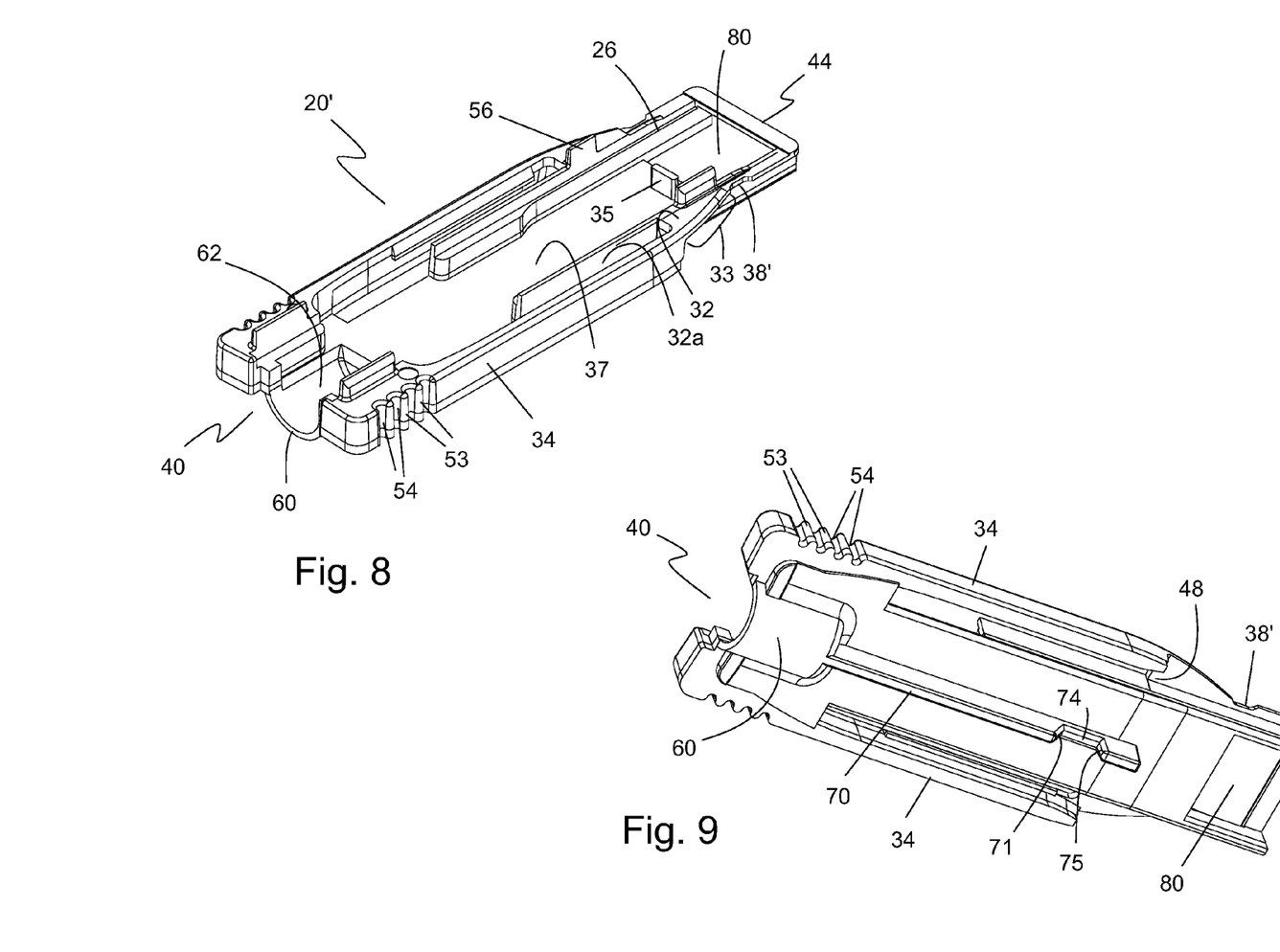
FIG. 8 is a perspective, top view of another embodiment of the lancet carrier of the present invention showing a bottom opening adjacent the closed end of the lancet carrier.
FIG. 9 is perspective, bottom view of the embodiment of the lancet carrier of the present invention shown in FIG. 8.

FIGS. 8 and 9 illustrate another embodiment of the present invention showing a lancet carrier 20'. FIG. 8 is a perspective, top view of lancet carrier 20'. Lancet carrier 20' includes all of the features described in lancet carrier 20 shown in FIGS. 2 and 3, but with a couple of additional and optional features. The first feature is a bottom opening 80 located adjacent body closed end 44. Bottom opening 80 exposes a portion of a bottom surface of sensor strip 300 opposite the electrical connector pads 322. This feature allows the optional inclusion of a means for the meter to identify the analyte that the sensor strip 300 can measure when a corresponding structure is incorporated in sensor strip 300. This is more clearly explained later. Incorporating bottom opening 80 in lancet carrier 20' requires placing anchoring tab 35 further away from closed end 44 as shown in FIG. 8 or a different structure to secure the anchor end of a lancet must be devised.

A second feature is the inclusion of a shelf slot 32a in shelf 32 that extends rearwardly from side openings 29, 31 towards closed end 44 and terminates at or within transition zone 33. Shelf slot 32a accommodates a piston cocking tab 710 of an optional re-use prevention component 700 discussed below. FIG. 9 is a bottom perspective view of the lancet carrier 20' shown in FIG. 9. Driver slots 48 are more clearly illustrated as being formed between side walls 28, 30 and wall portion 34.

Figure 10:
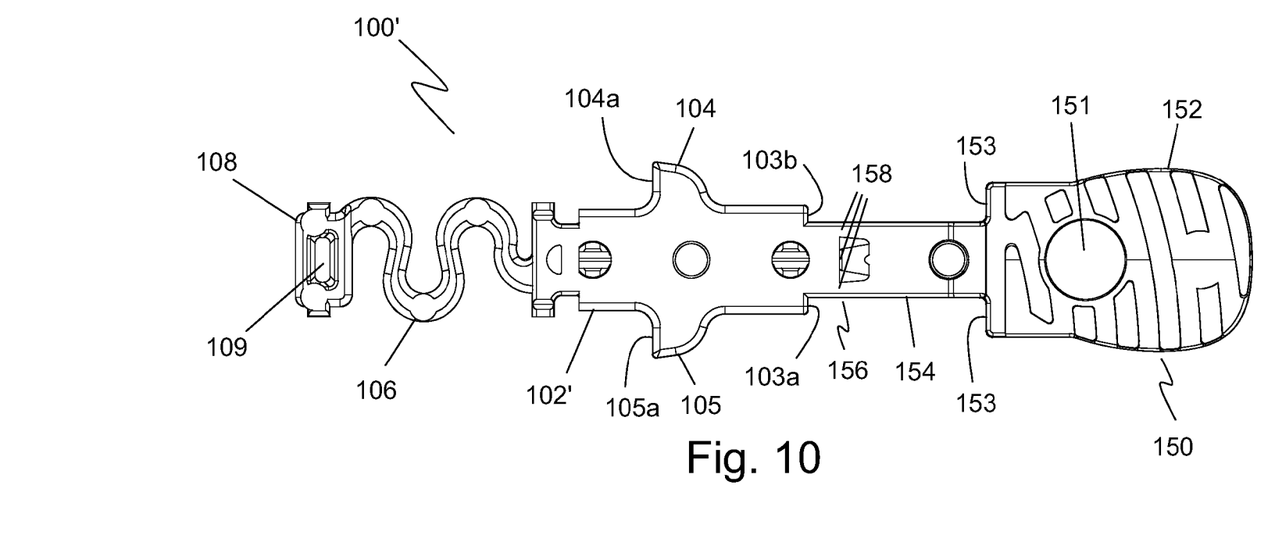
FIG. 10 is a top plan view of another embodiment of the lancet assembly of the present invention showing a lancet with a shorter lancet body for use with the lancet carrier embodiment shown in FIGS. 8 and 9.

Turning now to FIG. 10, there is illustrated a top plan view of another embodiment of the lancet of the present invention for use with lancet carrier 20' shown in FIGS. 8 and 9. A lancet 100' includes a lancet body 102' having first and second drive wings 104, 105, a biasing member 106, a lancet needle 140 (shown in FIG. 5), and an optional needle safety cap 150. Compared to lancet body 102 in FIG. 4, lancet body 102' is shorter since the retaining flange 35 is further away from closed end 44 of lancet carrier 20'. Optional needle safety cap 150 includes an optional tab capturing opening 151. The purpose of tab capturing opening 151 will be explained later. Biasing member 106 is directly connected to lancet body 102' on one end and includes an anchoring component 108 at the opposite end. Anchoring component 108 preferably includes a through-opening 109 that receives a retaining flange 35 of lancet carrier 20'. Anchoring component 108 fixes one end of lancet 100' so that biasing member 106 functions as intended, which is to pull the lancet body 102' and lancet needle 140 back into a retracted orientation within lancet carrier 20' after having been stretched during the extension to the exposed piercing orientation by the driver piston (not shown), which is incorporated within the meter (not shown). As illustrated in FIGS. 1, 4 and 10, safety cap 150 has a wider portion 152 that abruptly changes to a narrower portion 154. Narrower portion 154 is sized to slidably fit within a body opening 40a of body open end 40 of lancet carrier 20'. Narrower portion 154 is attached to lancet body 102 by a frangible connection 156. Frangible connection 156 preferably has three, separate neck portions 158 that are forcibly separated by a user from lancet body 102 to expose the piercing end 142 of lancet needle 140. As previously disclosed, safety cap 150 has a butting surface 153 at the transition between wider portion 152 and narrower portion 154 that prevents compression of biasing member 106 when lancet 100' is mounted within lancet carrier 20'. First and second drive wings 104, 105 also have wing butt surfaces 104a and 105a, respectively, that also prevent compression of biasing member 106 when lancet 100' is mounted within lancet carrier 20'.

Figure 11:
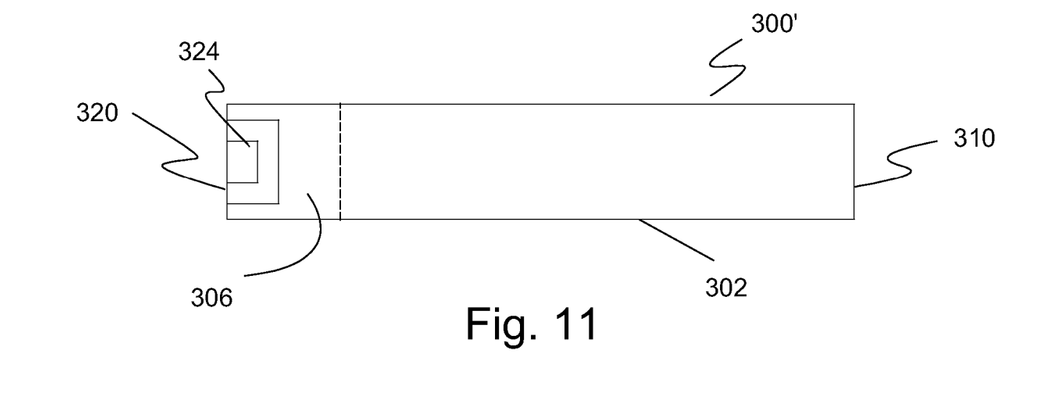
FIG. 11 is a bottom plan view of another embodiment of a sensor strip of the present invention showing a sensor identification structure on or in a bottom surface opposite the electrical connector pads at the electrical connector end.

FIG. 11 illustrates a bottom view of another embodiment of the sensor strip of the present invention for use with lancet carrier 20'. A sensor strip 300' includes an elongated body 302 with a sample receiving end 310 and a connector end 320. Connector end 320 has one or more electrical contact pads 322 on a top surface (not shown) for coupling the analyte electrodes to a meter (not shown). Sample receiving end 310 includes as previously disclosed and illustrated in FIG. 6 a sample inlet 312, a sample chamber 314 that contains the analyte measuring electrodes (not shown) within a capillary-sized, elongated tube, a vent 316 through which air escapes as it is displaced within sample chamber 314 when a sample is applied to sample inlet 312 that fills sample chamber 314 by capillary action, and an optional notch 318 incorporated within the roof of sample chamber 314 at sample receiving end 310. The novel feature incorporated in sensor strip 300' includes an identification structure 324 or pattern on a bottom surface 306. Identification structure 324 may be one or more of notches, channels, indents, raised surfaces, electrically conductive traces or lack thereof, and/or combinations thereof that are predefined for a particular strip sensor that measures a particular analyte or combination of analytes. Identification structure 324 may be integrally formed in the bottom of sensor strip 300' or added after sensor strip 300' is made. As an example, one pattern would represent a glucose measuring strip while another pattern would represent a lactate measuring strip and so on for each different type of analyte or combination of analytes. Each type of analyte measurement or specific combinations would have a unique pattern assigned enabling the meter to recognize the type of analyte sensor strip being connected to the meter. The meter would automatically select appropriate electronic circuits, programs and/or algorithms embedded within the meter to use with the sensor strip.

Figures 12, 13:
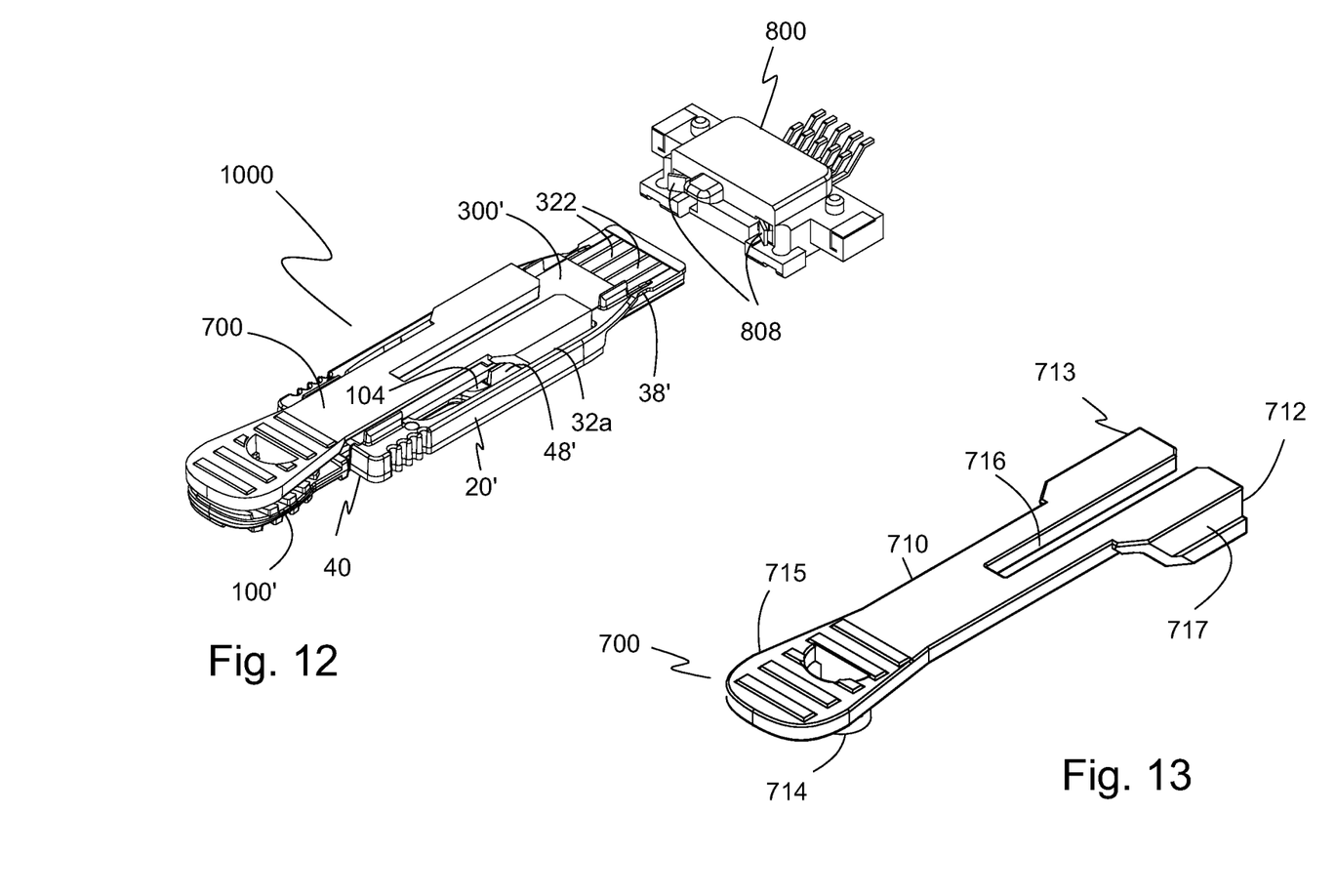
FIG. 12 is a perspective, top view of another embodiment of the present invention showing a lancet sensor cartridge with a re-use prevention component and one embodiment of a strip-receiving electrical connector that is mounted in a meter.
FIG. 13 is a perspective, top view of the embodiment of the re-use prevention component in FIG. 12 showing the driver piston flange.

FIG. 12 is a perspective view of another embodiment of a lancet cartridge of the present invention. Lancet sensor cartridge 1000 is a single, disposable, one-time use, integrated analytical device that combines a needle component or lancet 20' for lancing a specimen and an analyte measuring sensor strip 300' for receiving a fluid sample from the lanced specimen. Lancet cartridge 1000 is used in conjunction with a meter by inserting the lancet sensor cartridge 1000 into a cartridge receiving port on the meter and encasing one embodiment of a strip-receiving electro-mechanical connector 800. Connector 800 has at least one biasing retention tab 808 that is received in side notch 38' of lancet carrier 20'. A lancet driver assembly (not shown) is enabled, which when activated, engages the needle component to perform the specimen lancing function. The meter has an electrical coupler or strip-receiving electro-mechanical connector 800 that electrically connects to the sensor strip in order to make the analyte measurement but also mechanically engages lancet cartridge 1000. The electrical coupler will be described more fully later. In this embodiment, lancet cartridge 1000 also incorporates a re-use prevention component 700 that cooperates and engages with a driver piston component within the meter. Re-use prevention component 700 is removably coupled to lancet carrier 20' as the top-most component layer in the lancet cartridge 1000 with a portion extending beyond lancet carrier open end 40.

FIG. 13 is a perspective view of one embodiment of re-use prevention component 700. Re-use prevention component 700 in this embodiment is a removable, elongated, piston cocking tab 710 having at least one driver piston engageable surface 712 located at a first tab end 713 and a needle cap interlocking mechanism 714 at or near a second tab end 715. Piston cocking tab 710 may optionally include an alignment notch 716, which may cooperate with an alignment tab within the meter housing to which the lancet cartridge 1000 is coupled.

Piston cocking tab 710 includes a piston flange 717 that extends laterally and downwardly from cocking tab 71 at the first tab end 73 with the piston engageable surface 72 and that extends laterally and downwardly into piston channel 48 behind first drive wing 104. Piston flange 717 includes driver piston engageable surface 712. Needle cap interlocking mechanism 714 extends through tab capture opening 151 of needle safety cap 150 and interlocks piston cocking tab 710 with needle safety cap 150. When lancet cartridge 1000 is inserted into a meter housing having an appropriate lancet driver mechanism, the driver piston engageable surface 712 engages the lancet driver piston and pushes the lancet driver piston into an armed position. When needle safety cap 150 is removed from lancet cartridge 1000 after lancet cartridge 1000 is inserted into the meter housing and the piston cocking tab 710 has armed the lancet driver piston within the meter housing, piston cocking tab 710 is also simultaneously removed from lancet cartridge 1000 since it is interlocked with needle safety cap 150. The removal of piston cocking tab 710 from lancet cartridge 1000 removes the cocking mechanism that arms the lancet driver piston situated in the meter housing.

Figure 14:
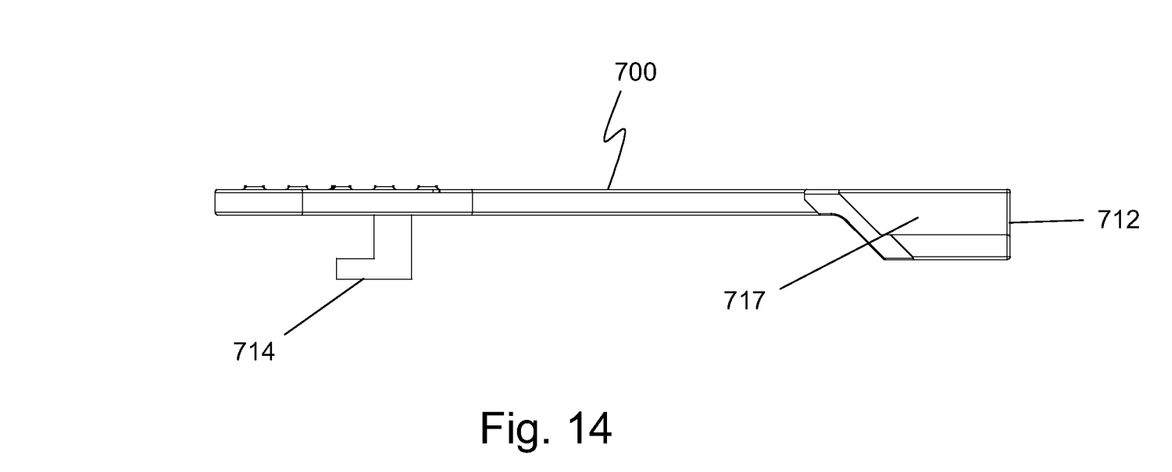
FIG. 14 is a side view of the re-use prevention component in FIG. 13 showing the needle cap interlocking mechanism.

FIG. 14 is a side view of re-use prevention component 700 shown in FIG. 13. Needle cap interlocking mechanism 714 is more clearly shown as a depending L-shaped flange that interconnects with tab capturing opening 151 of lancet 100'.

Figure 15:
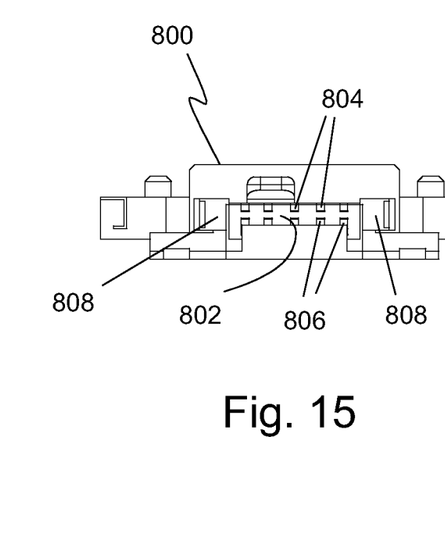
FIG. 15 is a front, plan view of the strip-receiving electrical connector in FIG. 12 showing the electro-mechanical contacts and the strip identification members.

FIG. 15 is a front view of one embodiment of a strip-receiving electro-mechanical connector 800. Connector 800 includes a strip receiving port 802 that houses a plurality of electro-mechanical contacts 804 and a plurality of strip identification members 806. Electro-mechanical contacts 804 are biased to maintain contact with electrical contact pads 322 of sensor strip 300' for making the analyte measurement. Strip identification members 806 maintain contact with identification structure 324 on bottom surface 306 of sensor strip 300'. As previously mentioned, the mating of identification structure 324 with strip identification members 806 initiates a particular signal (mechanical, electrical, optical and/or magnetic) that is interpreted by the meter to enable the meter to identify the type of measurement(s) that the inserted strip is capable of performing and to enable the meter to automatically select the proper programs, algorithms, measurement criteria, and the like for use with the inserted strip.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A lancet carrier for an integrated lancet sensor cartridge incorporating a lance cover, the lancet carrier comprising:
   an elongated body with a bottom, an open top, a body open end and a body closed end;
   a lancet-receiving recess with a recess bottom surface, the recess extending between the body open end and the body closed end; and
   a trough-forming member forming a trough with a trough wall, a trough open end in communication with the body open end and a trough closed end transverse to the trough wall, the trough closed end directly connected to the bottom of the elongated body, the trough-forming member longitudinally extending continuously a predefined distance along the bottom from the body open end and terminating in a transverse wall at the trough closed end and below the bottom, the trough replacing a portion of the recess bottom surface at the body open end wherein the lancet-receiving recess is stationary relative to the trough-forming member.

2. The lancet carrier of claim 1 wherein the trough is semi-circular.

3. The lancet carrier of claim 1 further comprising a plurality of transverse ridges and valleys formed in an outside surface of a side of the lancet carrier adjacent the body open end.

4. The lancet carrier of claim 1 further comprising an external bottom rib connected to the trough-forming member and extending longitudinally along a major portion of an outside bottom surface of the lancet carrier, and a carrier retaining notch formed laterally in the external bottom rib and having a carrier locking surface transverse to the longitudinal axis of the external bottom rib.

5. The lancet carrier of claim 1 further comprising an aperture formed in the bottom adjacent the body closed end and configured to expose one or more electrical connector pads of a sensor strip disposed on or combined with the lancet carrier.

6. A lancet carrier for an integrated lancet sensor cartridge, the lancet carrier comprising:
   an elongated body with a bottom, an open top, a body open end and a body closed end;
   a lancet-receiving recess with a recess bottom surface, the recess extending between the body open end and the body closed end; and
   an external bottom rib directly connected to and centered on the bottom of elongated body and extending longitudinally along and parallel to a major portion of an outside bottom surface of the lancet carrier, and a carrier retaining notch formed laterally in the external bottom rib and having a carrier locking surface transverse to the longitudinal axis of the external bottom rib, the carrier locking surface engageable with a cartridge lock of a meter to prevent longitudinal movement of the lancet carrier when a lancet of the integrated lancet sensor cartridge is operated.

7. The lancet carrier of claim 6 further comprising a plurality of transverse ridges and valleys formed in an outside surface of a side of the lancet carrier adjacent the body open end.

8. The lancet carrier of claim 6 further comprising a trough-forming member forming a trough with a trough wall, a trough open end in communication with the body open end and a trough closed end transverse to the trough wall wherein the trough closed end directly connects to the bottom of the elongated body, the trough-forming member longitudinally extending a predefined distance along the bottom from the body open end and terminating in a transverse wall at the trough closed end below the bottom, the trough replacing a portion of the recess bottom surface at the body open end wherein the lancet-receiving recess is stationary relative to the trough-forming member.

9. The lancet carrier of claim 8 wherein the trough is semi-circular.

10. The lancet carrier of claim 6 further comprising an aperture formed in the bottom adjacent the body closed end that is opposite the body open end and configured to expose one or more electrical connector pads of a sensor strip disposed on or combined with the lancet carrier.

11. A method of reducing damage to a sensor in an integrated lancet sensor cartridge having a lancet carrier with an elongated recess containing a lancet, the method comprising:

forming a lancet carrier having a trough-forming member with a trough wall, a trough open end and a trough closed end transverse to the trough wall, the trough closed end directly connected to a bottom of the lancet carrier, wherein the trough-forming member longitudinally extends continuously a predefined distance along a bottom of the lancet carrier from a carrier open end and terminating in a transverse wall at the trough closed end and below the bottom wherein a trough formed by the trough-forming member replaces a portion of a bottom surface of the recess adjacent the open end and wherein the elongated recess is stationary relative to the trough-forming member.

* * * * *